(12) United States Patent
Kim et al.

(10) Patent No.: US 10,139,323 B2
(45) Date of Patent: Nov. 27, 2018

(54) APPARATUS FOR SEPARATING MICRO-PARTICLES

(71) Applicants: Samsung Electronics Co., Ltd., Suwon-si, Gyeonggi-do (KR); University-Industry Cooperation Group of Kyung Hee University, Yongin-si, Gyeonggi-do (KR)

(72) Inventors: Minseoks Kim, Yongin-si (KR); Sungyoung Choi, Yongin-si (KR)

(73) Assignees: SAMSUNG ELECTRONICS CO., LTD., Suwon-si (KR); UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 434 days.

(21) Appl. No.: 14/838,025

(22) Filed: Aug. 27, 2015

(65) Prior Publication Data

US 2016/0161378 A1 Jun. 9, 2016

(30) Foreign Application Priority Data

Dec. 8, 2014 (KR) ........................ 10-2014-0175372

(51) Int. Cl.
*G01N 1/40* (2006.01)
*B01L 3/00* (2006.01)

(52) U.S. Cl.
CPC ...... *G01N 1/4077* (2013.01); *B01L 3/502753* (2013.01); *B01L 2200/0652* (2013.01);
(Continued)

(58) Field of Classification Search
None
See application file for complete search history.

(56) References Cited

U.S. PATENT DOCUMENTS 2,724,686 A * 11/1955 Nicholson ................ B01J 8/189
208/150
2,792,114 A * 5/1957 Kidwell .................... B03B 5/00
209/139.1
(Continued)

FOREIGN PATENT DOCUMENTS

JP 2012-100625 A 11/2010
KR 10-0907213 A 6/2009
(Continued)

OTHER PUBLICATIONS

Huang et al., "Continuous Particle Separation Through Deterministic Lateral Displacement", *Science*, 304: 987-990 (2014).
(Continued)

*Primary Examiner* — Jill A Warden
*Assistant Examiner* — Brittany I Fisher
(74) *Attorney, Agent, or Firm* — Leydig, Voit & Mayer, Ltd.

(57) ABSTRACT

An apparatus for separating micro-particles includes a channel through which a fluid flows, and a separating part protruding into the channel and including a slanted element inclined toward a length direction of the channel and a vertical element perpendicular to the length direction of the channel.

18 Claims, 12 Drawing Sheets

(52) U.S. Cl.
CPC ............... *B01L 2300/0816* (2013.01); *B01L 2300/0864* (2013.01); *B01L 2400/0487* (2013.01); *B01L 2400/086* (2013.01)

(56) References Cited

U.S. PATENT DOCUMENTS

| | | | |
|---|---|---|---|
| 5,765,393 A * | 6/1998 | Shlak | F25B 39/02 |
| | | | 165/146 |
| 7,333,859 B2 | 2/2008 | Rinaldi et al. | |
| 7,472,794 B2 | 1/2009 | Oakey et al. | |
| 8,071,054 B2 * | 12/2011 | Oh | B01L 3/502761 |
| | | | 422/502 |
| 8,304,230 B2 * | 11/2012 | Toner | B01L 3/502746 |
| | | | 422/414 |
| 8,585,971 B2 * | 11/2013 | Huang | B01L 3/502746 |
| | | | 422/50 |
| 2005/0106756 A1 * | 5/2005 | Blankenstein | B01L 3/502753 |
| | | | 436/523 |
| 2009/0107909 A1 * | 4/2009 | Kotera | B01L 3/502753 |
| | | | 210/513 |
| 2009/0208372 A1 * | 8/2009 | Mott | B01L 3/502776 |
| | | | 422/68.1 |
| 2011/0259834 A1 * | 10/2011 | Lee | B01J 19/0093 |
| | | | 210/749 |
| 2012/0103427 A1 * | 5/2012 | Park | B01F 5/0646 |
| | | | 137/3 |
| 2012/0261356 A1 * | 10/2012 | Tsutsui | B01L 3/502761 |
| | | | 210/767 |
| 2014/0087466 A1 * | 3/2014 | Ligler | B01J 19/0093 |
| | | | 435/400 |
| 2016/0090586 A1 | 3/2016 | Kim et al. | |

FOREIGN PATENT DOCUMENTS

| | | |
|---|---|---|
| KR | 10-1133288 A | 7/2010 |
| KR | 10-1097357 A | 1/2011 |
| KR | 2011-0031285 A | 3/2011 |
| KR | 2012-0113533 A | 10/2012 |

OTHER PUBLICATIONS

Mishima et al, "The 'Optical Funnel'. A Technique for Measuring a Microorganism's Power", *Analytical Chemistry*, 70 (16) 3513-3515 (1998).

Rodier et al., "Four faces of cellular senescence", *Jour. Cell. Biol.*, 192(4): 547-556 (2011).

Wang et al., "Cell Separation by Dielectrophoretic Field-flow-fractionation", *Analytical Chemistry*, 72 (4): 832-839 (2000).

Choi et al. "Continuous hydrophoretic separation and sizing of microparticles using slanted obstacles in a microchannel," *Lab Chip*, 7, pp. 890-897 (2007).

Choi et al. "Sheathless Focusing of Microbeads and Blood Cells Based on Hydrophoresis," *Small*, 4, No. 5, pp. 634-641 (2008).

Choi et al. "Microfluidic Self-Sorting of Mammalian Cells to Achieve Cell Cycle Synchrony by Hydrophoresis,", *Analytical Chemistry*, vol. 81, No. 5, pp. 1964-1968 (2009).

* cited by examiner

APPARATUS FOR SEPARATING MICRO-PARTICLES

RELATED APPLICATION

This application claims the benefit of Korean Patent Application No. 10-2014-0175372, filed on Dec. 8, 2014, in the Korean Intellectual Property Office, the disclosure of which is incorporated by reference herein in its entirety.

BACKGROUND

1. Field

The present disclosure relates to apparatus and methods for separating micro-particles.

2. Description of the Related Art

Along with recent advances in life sciences, more target substances are being analyzed for developing new drugs and obtaining accurate medical diagnoses. Before molecules of biological samples are analyzed, the biological samples may be pretreated to separate critical molecules and cells hindering the analysis.

In the related art, centrifugal separators are used to separate cells from suspensions. However, centrifugal separators require expensive equipment and are not easy to carry. That is, it is difficult to use centrifugal separators in specific situations such as emergency situations.

In addition, cell separating devices based on microfluidic techniques such as inertial fluidics or dielectrophoresis have been developed. However, the efficiency of such cell separating devices varies with the velocity of a fluid. For example, the cell separating efficiency of dielectrophoretic devices decreases as the velocity of the fluid increases, and the cell separating efficiency of inertial fluidic devices decreases as the velocity of a fluid decreases.

SUMMARY

Provided are an apparatus and method for separating micro-particles according to the size thereof.

Provided are an apparatus and method for separating micro-particles regardless of the velocity of a fluid.

Additional aspects will be set forth in part in the description which follows and, in part, will be apparent from the description, or may be learned by practice of the presented exemplary embodiments.

According to an aspect of an exemplary embodiment, an apparatus for separating micro-particles includes: a channel through which a fluid flows; and a separating part protruding into the channel and including a slanted element inclined toward a length direction of the channel and a vertical element perpendicular to the length direction of the channel. The fluid flow may be in the direction of the length direction of the channel or opposite the length direction of the channel.

Both ends of the separating part may be connected to sidewalls of the channel.

A length direction of the slanted element may be inclined toward the length direction of the channel.

The fluid may include critical particles, e.g., target particles to be separated, and a distance between the slanted element and a surface of the channel may be greater than a diameter of the critical particles and equal to or smaller than twice the diameter of the critical particles.

The slanted element may have a height greater than a distance between the slanted element and a surface of the channel.

The slanted element and the vertical element may have the same height.

The slanted element may include first and second sub-slanted elements that are symmetric with respect to a center axis of the channel.

The vertical element may include: a first sub-vertical element between the first sub-slanted element and a sidewall of the channel; a second sub-vertical element between the second sub-slanted element and a sidewall of the channel; and a third sub-vertical element between the first and second sub-slanted elements.

The separating part may include: a first separating part or component including a first slanted element and a first vertical element; and a second separating part or component separate from the first separating part in the length direction of the channel and including a second slanted element and a second vertical element.

The first slanted element and the second slanted element may overlap each other in some regions, e.g., regions along the length direction of the channel, and may not overlap each other in other regions.

Overlapping regions of the first slanted element and the second slanted element may have a length ranging from ⅓ to ⅔ of a length of the first slanted element.

The first slanted element may include a first sub-slanted element inclined in a first direction, and the second slanted element may include a second sub-slanted element inclined in the first direction.

An arrangement direction of the second sub-slanted element relative to the first sub-slanted element may have a sign opposite to a sign of the first direction.

The first sub-slanted element and the second sub-slanted element may have the same degree of slant (e.g., slant angle) and/or the same length.

If the first separating part is adjacent to an end of the channel, the first slanted element may be in contact with a sidewall of the channel or may be in a center region of the channel.

According to an aspect of another exemplary embodiment, an apparatus for separating micro-particles, the apparatus including: a channel through which a fluid flows; and a plurality of slanted elements protruding into the channel and inclined toward a length direction of the channel (e.g., at an angle relative to a center axis of the channel), the slanted elements being separate from each other in the length direction of the channel, wherein the slanted elements are sequentially arranged in a first direction different from the length direction of the channel.

The slanted elements may have the same slant direction, e.g., angle relative to the center axis of the channel.

The first direction and the slant direction may have opposite signs.

Two neighboring slanted elements of the plurality of slanted elements may overlap each other in some regions and may not overlap each other in other regions.

If particles having a diameter equal to or greater than ½ of a distance between at least one of the slanted elements and a surface of the channel but smaller than the distance are included in the fluid and introduced into the apparatus, the apparatus may control a moving direction of the particles so that the particles may have directivity or directionality, whereby a concentration of particles may be controlled at an output end of the channel.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
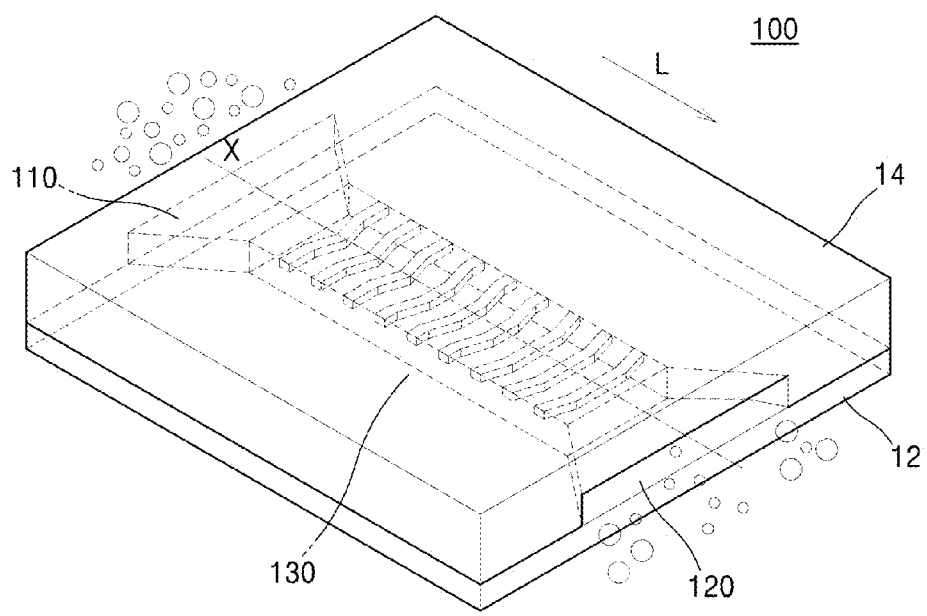
FIG. 1 is a perspective view illustrating an apparatus for separating micro-particles according to an exemplary embodiment.

Reference will now be made in detail to exemplary embodiments, examples of which are illustrated in the accompanying drawings. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Hereinafter, an apparatus and method for separating micro-particles according to the size of the micro-particles will be described in detail with reference to the accompanying drawings. In the drawings, like reference numbers refer to like elements, and also the size of each element may be exaggerated for clarity of illustration.

It will be understood that although the terms "first" and "second" are used herein to describe various elements, these elements should not be limited by these terms. These terms are only used to distinguish one element from other elements.

According to exemplary embodiments, a micro-particle separating apparatus may be used for dividing particles contained in a fluid into particles having a size equal to or larger than a critical size and particles having a size smaller than the critical size and then discharging the particles through an outlet in a state in which the distribution of the particles having a size smaller than the critical size and the distribution of the particles having a size equal to or larger than the critical size are concentrated in certain regions of the outlet.

In the exemplary embodiments, particles may refer to particles of various biological substances. Examples of particles of biological substances may include cells or biomolecules. The cells may refer to various cells such as cancer cells, red blood cells, white blood cells, phagocytes, animal cells, or plant cells. The biomolecules may refer to various molecules of living bodies such as proteins, lipids, or nucleic acids including DNAs and RNAs. However, the biomolecules are not limited thereto. Examples of the biomolecules may include aptamers, antigens, antibodies, enzymes, enzyme substrates, enzyme inhibitors, receptors, and receptor ligands.

The micro-particle separating apparatus may be used for pre-treatments before diagnostic devices are used and may be applied to various fields of biological research. The micro-particle separating apparatus may be used for separating different kinds of particles according to the sizes thereof. For example, the micro-particle separating apparatus may be used to separate blood corpuscles from plasma or a cell culture medium from cells. However, the micro-particle separating apparatus is not limited thereto.

According to the exemplary embodiments, the micro-particle separating apparatus may be used to separating cells having the same type but different aging degrees. In the field of aging research, it has been difficult to find main factors of aging due to the effect of ensemble averaging caused by cell heterogeneity. Therefore, it is necessary to separate a homogeneous aging cell population.

Aging cells obtained using a dish may be separated according to the sizes thereof so as to measure the sizes of the cells and the amounts of accumulated waste products according to the sizes of the cells. Results of such a measurement showed that large cells have relatively large amounts of accumulated waste products and are more aged. When such aging cells are refined and are separated, the micro-particle separating apparatus of the exemplary embodiments may be used.

Figure 2:
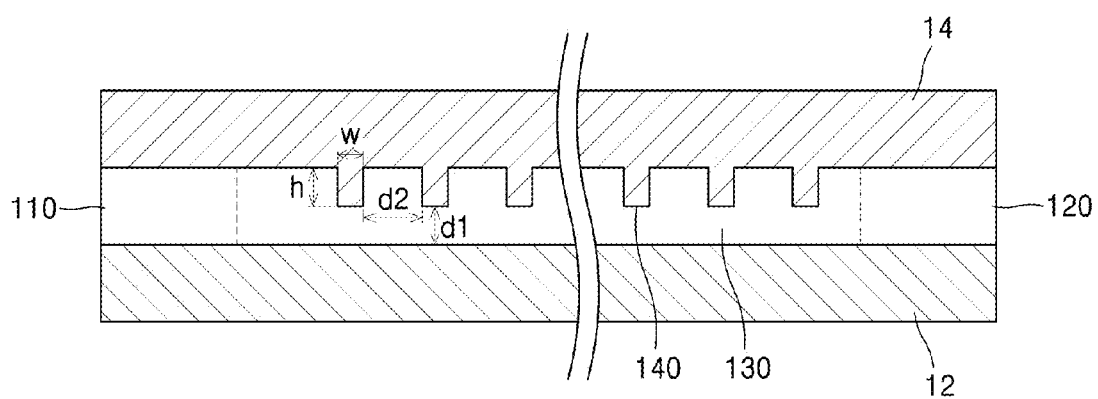
FIG. 2 is a cross-sectional view illustrating the micro-particle separating apparatus illustrated in FIG. 1.
Figure 3A:
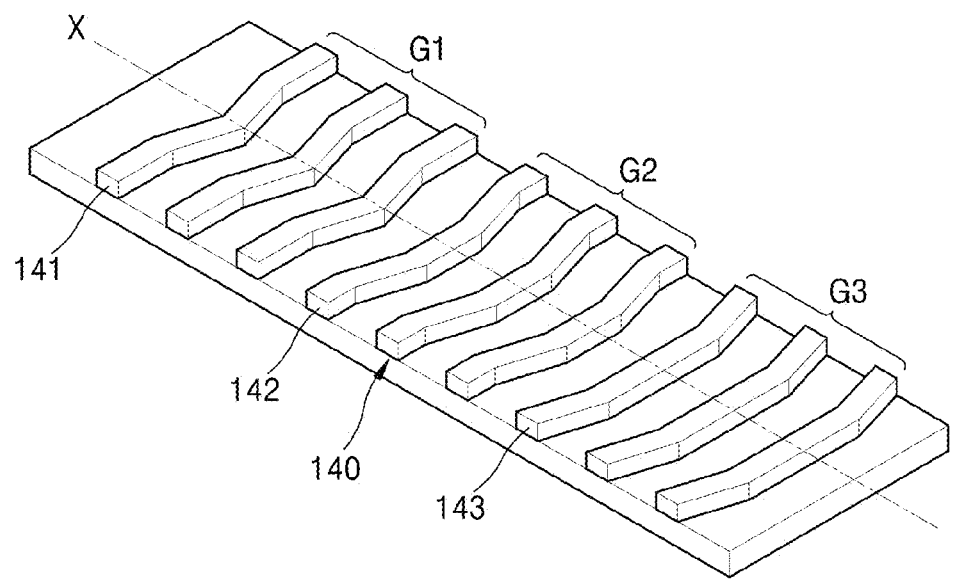
FIG. 3A is a bottom perspective view illustrating a first substrate illustrated in FIG. 1.
Figure 3B:
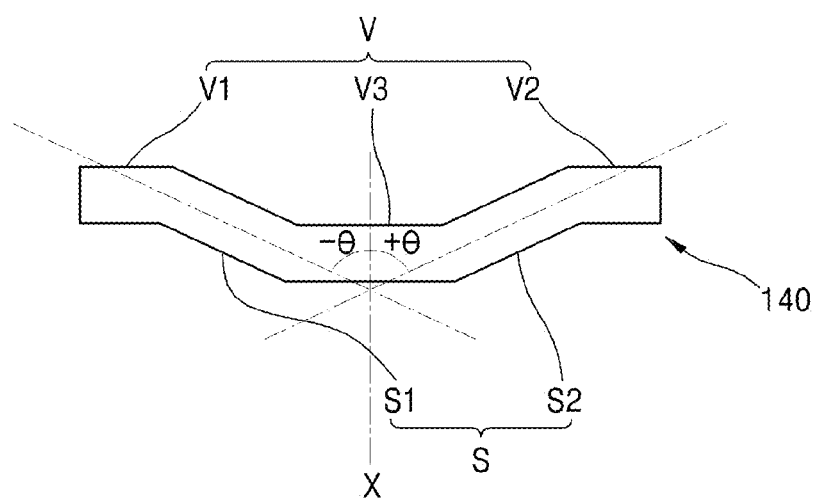
FIG. 3B is a view illustrating an exemplary separating part according to the exemplary embodiment.

FIG. 1 is a perspective view illustrating an apparatus 100 for separating micro-particles according to an exemplary embodiment. FIG. 2 is a cross-sectional view illustrating the micro-particle separating apparatus 100 illustrated in FIG. 1. FIG. 3A is a bottom perspective view illustrating a first substrate 12 illustrated in FIG. 1, and FIG. 3B is a view illustrating an exemplary separating part 140 according to the exemplary embodiment. Referring to FIGS. 1 to 3B, a micro-particle separating apparatus 100 may include an inlet 110 through which a fluid is introduced, an outlet 120 through which the fluid is discharged, a channel 130 between and connecting the inlet 110 and outlet 120 to allow the fluid to flow therethrough, and one or more separating parts 140 protruding from a surface of the channel 130 into the channel 130. The fluid may contain at least one kind of particles.

In the exemplary embodiment, the micro-particle separating apparatus 100 may be formed by joining a plurality of substrates having flat surfaces. For example, the micro-particle separating apparatus 100 may include: the first substrate 12 on which lower surfaces of the inlet 110, the outlet 120, and the channel 130 are formed; and a second substrate 14 having a lower surface on which the other regions of the inlet 110, the outlet 120, and the channel 130, and the separating parts 140 are formed. Upper surfaces of the inlet 110, the outlet 120, and the channel 130, and the separating parts 140 may be formed by etching regions of the lower surface of the second substrate 14. The micro-particle separating apparatus 100 may be formed by joining the etched lower surface of the second substrate 14 to an upper surface of the first substrate 12. Alternatively, the micro-particle separating apparatus 100 may be formed by joining three substrates.

The micro-particle separating apparatus 100 may be formed of a material that is chemically and biologically inactive. If it is intended to be used to observe variations in the distribution of particles, the micro-particle separating apparatus 100 may be formed of a transparent material. For example, the micro-particle separating apparatus 100 may be formed of a material such as a plastic material, glass, mica, silica, or a semiconductor wafer material. Examples of the plastic material may include: an acrylic material such as polymethylmethacrylate (PMMA); polysiloxane such as poly-dimethyl siloxane (PDMS); polycarbonate (PC); polyethylene such as linear low-density polyethylene (LLDPE), low-density polyethylene (LDPE), medium-density polyethylene (MDPE), or high-density polyethylene (HDPE); polyvinyl alcohol; very-low-density polyethylene (VLDPE); polypropylene (PP); acrylonitrile butadiene styrene (ABS); or cycloolefin copolymer (COO). However, the listed materials are examples. That is, the micro-particle separating apparatus 100 of the exemplary embodiments is not limited thereto.

In one embodiment, the inlet 110 may be tapered. For example, an exposed end of the inlet 110 may be larger than the other (inner) end of the inlet 110 connected to the channel 130 as shown in FIG. 1. The cross section of the inlet 110 may be gradually reduced in a direction from the exposed end to the other, inner end thereof. Since the exposed end of the inlet 110 is relatively large, a large amount of fluid may be introduced into the channel 130 through the inlet 110.

In one embodiment, the outlet 120 may also be tapered. For example, an inner end of the outlet 120 connected to the channel 130 may be smaller than the other end of the outlet 120 exposed to the outside as shown in FIG. 1. The cross section of the outlet 120 may be gradually increased in a direction from the inner end to the exposed end thereof. After passing through the channel 130, particles may be distributed according to the size thereof. The distance between particles having different sizes may be increased while the particles pass through the outlet 120, and thus particles having a certain size may be easily separated from particles having other sizes.

It may not be necessary to expose the inlet 110 and the outlet 120 to the outside. If the micro-particle separating apparatus 100 of the exemplary embodiment is a component of a particle analyzer, the inlet 110 may be connected to a part of the micro-particle separating apparatus 100, and the outlet 120 may be connected to a part of the particle analyzer.

The channel 130 may be disposed between the inlet 110 and the outlet 120. An end of the channel 130 may be connected to the inner end of the inlet 110, and the other end of the channel 130 may be connected to the inner end of the outlet 120. The width of the channel 130 may be about several tens of micrometers ($\mu m$) or more. The cross section of the channel 130 may be uniform. However, the channel 130 is not limited thereto.

For example, in an embodiment, the channel 130 may be tapered. In this embodiment, the cross section of the channel 130 may be increased from the end to the other end thereof. If the cross section of the channel 130 is increased as described above, the distance between particles having different sizes may be increased while the particles pass through the channel 130. Then, particles having a certain size may be easily separated. Hereinafter, a direction from the end of the channel 130 connected to the inlet 110 to the other end of the channel 130 connected to the outlet 120 will be referred to as a length direction L of the channel 130. Length direction L is also typically the flow direction of fluid in the channel 130.

The inlet 110, the channel 130, and the outlet 120 may have a common center axis X. The center axis X may be parallel with the moving direction of fluid. A fluid introduced into the micro-particle separating apparatus 100 may pass through the inlet 110, the channel 130, and the outlet 120 without changing its moving direction. Therefore, phenomena such as loss and accumulation of particles may minimally occur when a fluid flows.

The micro-particle separating apparatus 100 may include one or more separating parts 140 protruding from a surface of the channel 130 to the inside of the channel 130. In the channel 130, the separating parts 140 may be formed in a direction crossing the length direction L of the channel 130. Both ends of the separating parts 140 may be connected to sidewalls of the channel 130 as shown in FIG. 1.

The separating parts 140 may protrude toward a certain region of the channel 130. Referring to FIG. 2, a distance d1 between the surface of substrate 12 defining the channel 130 and the separating parts 140 may be determined according to the size of particles to be changed in the distribution thereof (hereinafter, such particles will be referred to as critical particles). For example, the distance d1 between the surface of substrate 12 defining the channel 130 and slanted elements S of the separating parts 140 may be greater than the diameter of critical particles P1 but equal to or smaller than twice the diameter of the critical particles P1.

In addition, the height h of the separating parts 140 may be greater than the distance d1 between the surface of the channel 130 and the separating parts 140. In addition, the distance d2 between the separating parts 140 may be equal to or smaller than twice the diameter of the critical particles P1, and the width W of the separating parts 140 may be equal to or smaller than the diameter of the critical particles P1. The above-mentioned ranges of the height h of the separating parts 140, the distance d2 between the separating parts 140, and the width W of the separating parts 140 are exemplary ranges, and the separating parts 140 are not limited thereto. For example, the height h of the separating parts 140, the distance d2 between the separating parts 140, and the width W of the separating parts 140 may range from about several micrometers ($\mu m$) to about 100 micrometers ($\mu m$) or more regardless of the diameter of the critical particles P1.

Referring to FIG. 2, the separating parts 140 protrude from an upper surface of the channel 130. However, the separating parts 140 may protrude from a lower surface of the channel 130. In addition, some of the separating parts 140 may protrude from the upper surface of the channel 130, and the other of the separating parts 140 may protrude from the lower surface of the channel 130.

FIG. 3B is a view illustrating an exemplary separating part 140. The separating part 140 may include: a slanted element S disposed on a region of a surface of the channel 130 and inclined toward the length direction L of the channel 130; and a vertical element V disposed on another region of the surface of the channel 130 in a direction perpendicular to the length direction L of the channel 130.

In FIG. 3B, the separating part 140 is illustrated as including the slanted element S and the vertical element V. However, the separating part 140 is not limited thereto. For example, the separating part 140 may include the slanted element but may not include the vertical element V. The slanted element S and the vertical element V may have the same height and the same width or different heights and widths. If the slanted element S and the vertical element V have the same height and the same width, particles may be efficiently separated. However particles may be separated even though the slanted element S and the vertical element V have different heights and widths. In FIG. 3B, the slanted element S and the vertical element V are connected to each other. However, the separating part 140 is not limited thereto. For example, the slanted element S and the vertical element V may be partially connected to each other or separate from each other.

The slanted element S may include a first sub-slanted element S1 and a second sub-slanted element S2 that are symmetric with respect to the center axis X of the channel 130. The first sub-slanted element S1 and the second sub-slanted element S2 may have the same degree of slant, θ, but different slant directions. In FIG. 3B, the separating part 140 is illustrated as having two sub-slanted elements S1 and S2. However, the separating part 140 may include only one sub-slanted element S1 or S2.

The slant degree θ may be an acute angle between the length direction of the sub-slanted element S1 or S2 and the center axis X of the channel 130. If the acute angle between the center axis X of the channel 130 and the length direction of the sub-slanted element S1 or S2 is clockwise from the center axis X of the channel 130, the slant direction of the sub-slanted element S1 or S2 is positive, and if the acute angle is counterclockwise, the slant direction is negative. The slanted directions and slant degrees of the sub-slanted elements S1 and S2, and the number of slanted elements S may be determined by factors such as the size of the channel 130 and the size of critical particles P1 to be separated.

The vertical element V may include: a first sub-vertical element V1 disposed between the first sub-slanted element S1 and a sidewall of the channel 130; and a second sub-vertical element V2 disposed between the second sub-slanted element S2 and the other sidewall of the channel 130. For example, an end of the first sub-vertical element V1 may be in contact with the sidewall of the channel 130, and the other end of the first sub-vertical element V1 may be in contact with the first sub-slanted element S1. In addition, an end of the second sub-vertical element V2 may be in contact with the second sub-slanted element S2, and the other end of the second sub-vertical element V2 may be in contact with the other sidewall of the channel 130. However, the vertical element V is not limited thereto. The vertical element V may further include a third sub-vertical element V3 disposed between the first sub-slanted element S1 and the second sub-slanted element S2. According to the position of the channel 130, the separating part 140 may include a vertical element V constituted by first and second sub-vertical elements V1 and V2, a vertical element V constituted by first to third sub-vertical elements V1 to V3, or a vertical element V constituted by a third sub-vertical element V3.

As shown in FIGS. 1 to 3A, a plurality of separating parts 140 may be arranged in the channel 130. The separating parts 140 may be separate from each other in the length direction L of the channel 130. The distance d2 between the separating parts 140 may be constant or varied. The shape of the separating parts 140 may be varied in the length direction L of the channel 130. All the separating parts 140 may have different shapes. Alternatively, the separating parts 140 may be grouped according to the shapes thereof, and separating parts 140 in a group (hereinafter referred to as a separation group) may have a shape different from the shape of separating parts 140 in another separation group.

For example, as shown in FIG. 3A, the micro-particle separating apparatus 100 may include first to third separation groups G1, G2, and G3. Separating parts 140 (hereinafter referred to as first separating parts 141) of the first separation group G1, separating parts 140 (hereinafter referred to as second separating parts 142) of the second separation group G2, and separating parts 140 (hereinafter referred to as third separating parts 143) of the third separation group G3 may have different shapes. In FIG. 3A, the number of separating parts 141, 142, or 143 of each separation group is three. However, the number of separating parts 141, 142, or 143 is not limited thereto. For example, more separating parts may be included in each separation group. Furthermore, in FIG. 3A, three separation groups are shown. However, the number of separation groups is not limited thereto. For example, three or more separation groups may be arranged.

Figure 4:
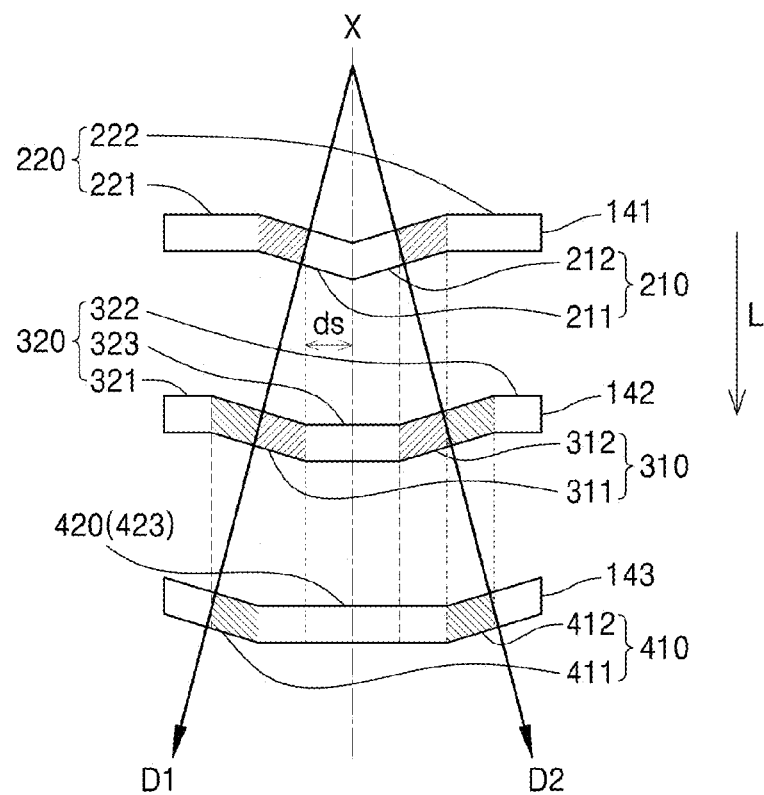
FIG. 4 is a reference view illustrating first to third separating parts illustrated in FIG. 3A.

FIG. 4 is a reference view illustrating first to third separating parts illustrated in FIG. 3A. Referring to FIG. 4, the first separating part 141 may include: first and second sub-slanted elements 211 and 212 connected to each other in a center region of the channel 130; a first sub-vertical element 221 disposed between the first sub-slanted element 211 and a sidewall of the channel 130; and a second sub-vertical element 222 disposed between the second sub-slanted element 212 and the other sidewall of the channel 130.

The second separating part 142 may include: first and second sub-slanted elements 311 and 312 separate from each other; a first sub-vertical element 321 disposed between the first sub-slanted element 311 and the sidewall of the channel 130; a second sub-vertical element 322 disposed between the second sub-slanted element 312 and the other sidewall of the channel 130; and a third sub-vertical element 323 disposed between the first sub-slanted element 311 and the second sub-slanted element 312.

The third separating part 143 may include: first and second sub-slanted elements 411 and 412; and a third sub-vertical element 423 disposed between the first and second sub-slanted element 411 and 412.

Although the first to third separating parts 141, 142, and 143 may have different shapes, slanted elements 210, 310, and 410 of the first to third separating parts 141, 142, and 143 may be symmetric with respect to the center axis X of the channel 130. In addition, corresponding sub-slanted elements of the first to third separating parts 141, 142, and 143 may have the same slant direction. For example, the first sub-slanted elements 211, 311, and 411 (hereinafter referred to as first corresponding sub-slanted elements 211, 311, and 411) of the first to third separating parts 141, 142, and 143 may have the same slant direction, and the second sub-slanted elements 212, 312, and 412 (hereinafter referred to as second corresponding sub-slanted elements 212, 312, and 412) of the first to third separating parts 141, 142, and 143 may have the same slant direction.

The slanted elements 210 and 310 or 310 and 410 of a neighboring pair of the first to third separating parts 141, 142, and 143 (for example, the first and second separating parts 141 and 142 or the second and third separating parts 142 and 143) may overlap each other in some regions and may not overlap each other in the other regions. For example, the first sub-slanted element 211 of the first separating part 141 and the first sub-slanted element 311 of the second separating part 142 may overlap each other in some regions and may not overlap each other in the other regions. The second sub-slanted element 212 of the first separating part 141 and the second sub-slanted element 312 of the second separating part 142 may overlap each other in some regions and may not overlap each other in the other regions. The length of an overlapping region of a sub-slanted element may be about ⅓ to about ⅔ of the length of the sub-slanted element.

In addition, corresponding sub-slanted elements such as the first corresponding sub-slanted elements 211, 311, and 411 or the second corresponding sub-slanted elements 212, 312, and 412 may be arranged in a constant arrangement direction D1 or D2. The arrangement direction D1 of the first corresponding sub-slanted elements 211, 311, and 411 and the arrangement direction D2 of the second corresponding sub-slanted elements 212, 312, and 412 may be inclined from the center axis X of the channel 130. For example, the arrangement direction D1 and slant direction of the first corresponding sub-slanted elements 211, 311, and 411 may have different signs. For example, following the length direction L of the channel 130, the first corresponding sub-slanted elements 211, 311, and 411 may be sequentially shifted in a direction from the center axis X of the channel 130 toward an edge of the channel 130, and the second corresponding sub-slanted elements 212, 312, and 412 may be sequentially shifted from the center axis X of the channel 130 to another edge of the channel 130.

Since sub-slanted elements corresponding to each other and neighboring each other (such as the first and second sub-slanted elements 211 and 311) are shifted in a direction from the center axis X of the channel 130 toward an edge of the channel 130 following the length direction L of the channel 130, a distance between the corresponding and neighboring sub-slanted elements (such as the first and second sub-slanted elements 211 and 311) measured in a direction away from the center axis X of the channel 130 may be defined as a shift distance ds. The separation groups G1, G2, and G3 may be arranged with the same shift distance ds therebetween. However, the separation groups G1, G2, and G3 are not limited thereto. For example, the separation groups G1, G2, and G3 may be arranged with different shift distances ds therebetween.

Figure 5:
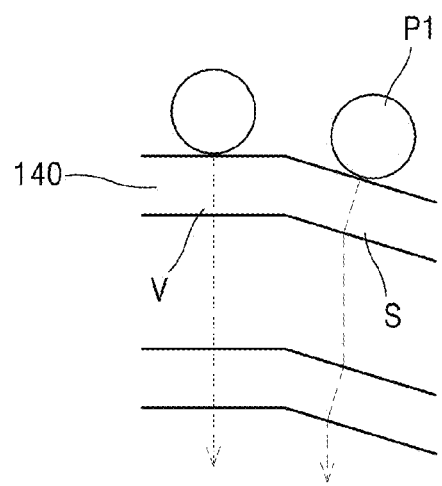
FIG. 5 is a reference view illustrating a moving path of critical particles passing across separating parts according to the exemplary embodiment.

Each of the slanted elements 210, 310, and 410 of the separating parts 141, 142, and 143 may control the moving direction of critical particles P1. FIG. 5 is a reference view illustrating a moving path of critical particles P1 passing across separating parts 140 according to the exemplary embodiment. Due to the slanted elements S of the separating parts 140, fluid undergoes secondary flows, and the moving direction of critical particles P1 is inclined opposite the slant direction of the slanted elements S. For example, if the slant direction of the slanted elements S is positive, the critical particles P1 move in a negatively slanted direction. However, when the critical particles P1 pass across the vertical elements V, the fluid does not undergo secondary flows, and thus the critical particles P1 randomly pass across the vertical elements V. Although particles P2 (non-critical particles) smaller than critical particles P1 pass across the slanted elements S or the vertical elements V, the non-critical particles P2 randomly move without regularity.

Therefore, the critical particles P1 move in a particular direction as the critical particles P1 pass across the slanted elements S, and thus the critical particles P1 may concentrated in certain regions of the outlet 120. For example, if the slant direction of a sub-slanted element is positive, the critical particles P1 move in a negatively slanted direction while passing across the sub-slanted element. In addition, if the slant direction of a sub-slanted element is negative, the critical particles P1 move in a positively slanted direction while passing across the sub-slanted element.

Figure 6A:
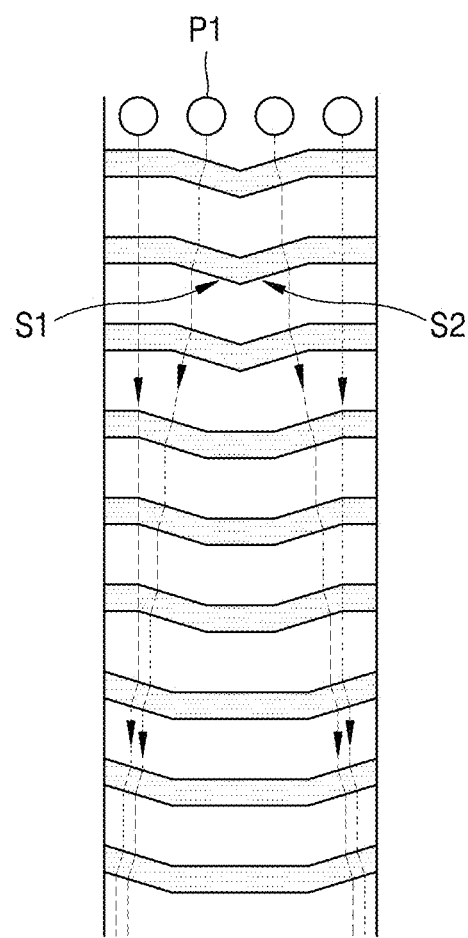
FIG. 6A is a schematic view illustrating moving paths of critical particles passing through the micro-particle separating apparatus illustrated in FIG. 1.
Figure 6B:
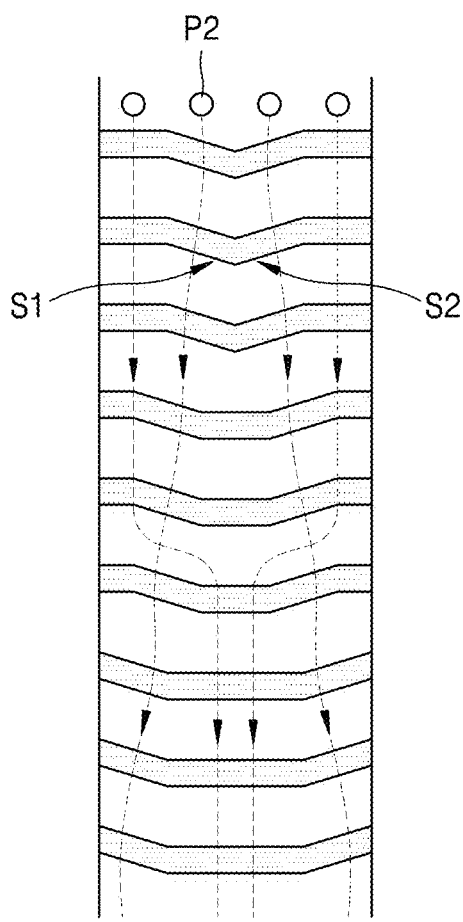
FIG. 6B is a schematic view illustrating moving paths of non-critical particles passing through the micro-particle separating apparatus illustrated in FIG. 1.

FIG. 6A is a schematic view illustrating moving paths of critical particles P1 passing through the micro-particle separating apparatus 100 illustrated in FIG. 1, and FIG. 6B is a schematic view illustrating moving paths of non-critical particles P2 passing through the micro-particle separating apparatus 100 illustrated in FIG. 1. Although a fluid in which critical particles P1 are uniformly dispersed is introduced into the channel 130, the critical particles P1 begin to have directivity or directionality while passing across the slanted elements S.

For example, as shown in FIG. 6A, the first sub-slanted elements S1 having a negative slant direction may be disposed in a left region of the channel 130 based on the center axis X of the channel 130, and the second sub-slanted elements S2 having a positive slant direction may be disposed in a right region of the channel 130 base on the center axis X of the channel 130. Critical particles P1 passing through the left region of the channel 130 are inclined to the left while passing across the first sub-slanted elements S1. The extent that the critical particles P1 are concentrated on a left edge side of the channel 130 is increased in proportion to the number of the first sub-slanted elements S1. Critical particles P1 passing through the right region of the channel 130 are inclined to the right while passing across the second sub-slanted elements S2. The extent that the critical particles P1 are concentrated on a right edge side of the channel 130 is increased in proportion to the number of the second sub-slanted elements S2. Therefore, although the distribution of the critical particles P1 is random before the critical particles P1 pass through the channel 130, the critical particles P1 are distributed densely at edge regions of the channel 130, that is, at edge regions of the outlet 120, after the critical particles P1 pass through the channel 130.

On the other hand, the moving direction of non-critical particles P2 having a random distribution and introduced into the channel 130 is not varied by the slanted elements S. Therefore, as shown in FIG. 6B, although the non-critical particles P2 pass across the slanted elements S, the non-critical particles P2 maintain its random distribution, and thus the distribution of the non-critical particles P2 is random after the non-critical particles P2 pass through the channel 130. However, since the distribution of the critical particles P1 is concentrated in the edge regions of the channel 130, the distribution ratio of the non-critical particles P2 to all the particles is varied to be high in a center region of the outlet 120.

Figure 7A:
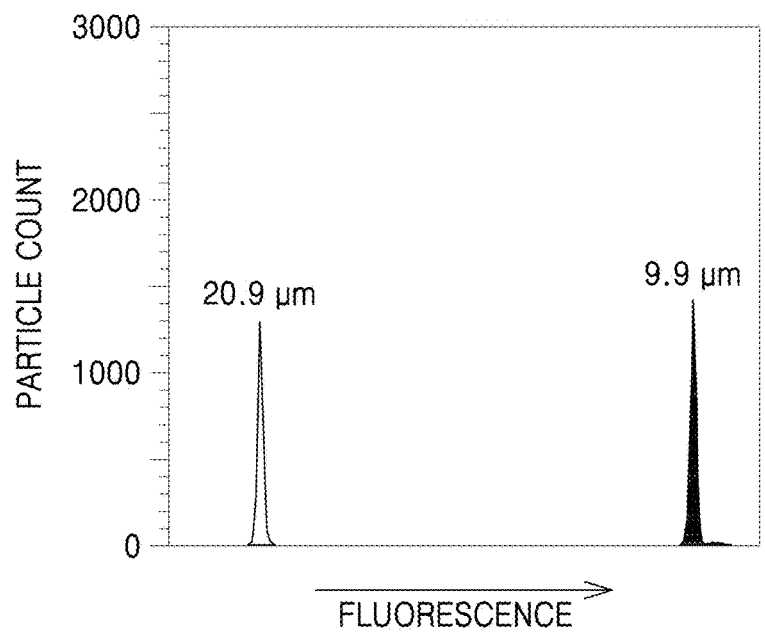
FIG. 7A is a graph illustrating the distribution of particles in a fluid introduced into the micro-particle separating apparatus of the exemplary embodiment.
Figure 7B:
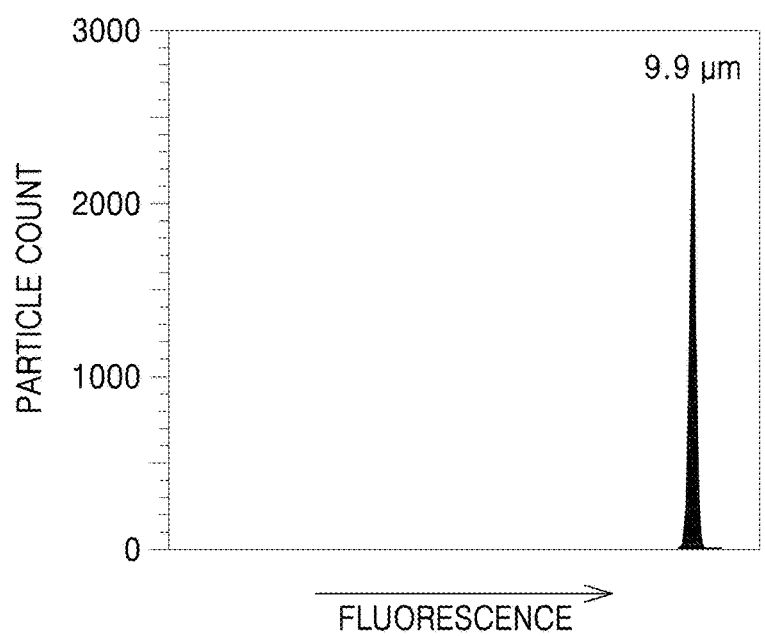
FIG. 7B is a graph illustrating the distribution of particles in the fluid after the fluid have passed through the micro-particle separating apparatus.

FIG. 7A is a graph illustrating the distribution of particles in a fluid introduced into the micro-particle separating apparatus 100 of the exemplary embodiment, and FIG. 7B is a graph illustrating the distribution of particles in the fluid after the fluid have passed through the micro-particle separating apparatus 100. The micro-particle separating apparatus 100 of the exemplary embodiment was fabricated such that the width and height of the channel 130 was about 550 µm and about 119 µm, respectively, and the number of the separating parts 140 in the channel 130 was 240. Six separation groups were arranged in the channel 130, and forty separating parts 140 were included in each separation group. The distance between the separating parts 140 and a surface of the channel 130 was about 39 µm, and the shift distance between the separation groups was about 70 µm. A red fluorescent material is applied to first particles having a diameter of about 9.9 µm, and no fluorescent material is applied to second particles having a diameter of about 20.9 µm. Since the distance between the separating parts 140 and a surface of the channel 130 was about 39 µm, particles having a diameter of about 19.5 µm or greater might be critical particles P1. That is, it was predicted that the second particles were critical particles P1. A fluid containing the first and second particles was introduced into the micro-particle separating apparatus 100.

As shown in FIG. 7A, the concentration of the first particles was about 52.8% in a center region of the inlet 110. While the fluid was passing through the channel 130 of the micro-particle separating apparatus 100, the second particles might be moved toward lateral sides of the channel 130 and discharged through edge regions of the outlet 120. Therefore, the concentration of the first particles discharged through a center region of the outlet 120 might be relatively increased. As shown in FIG. 7B, the concentration of the first particles discharged through the center region of the outlet 120 was relatively increased. The concentration of the first particles in the fluid discharged through the center region of the outlet 120 was about 98%. That is, particles were efficiently separated according to the size thereof.

Figure 8:
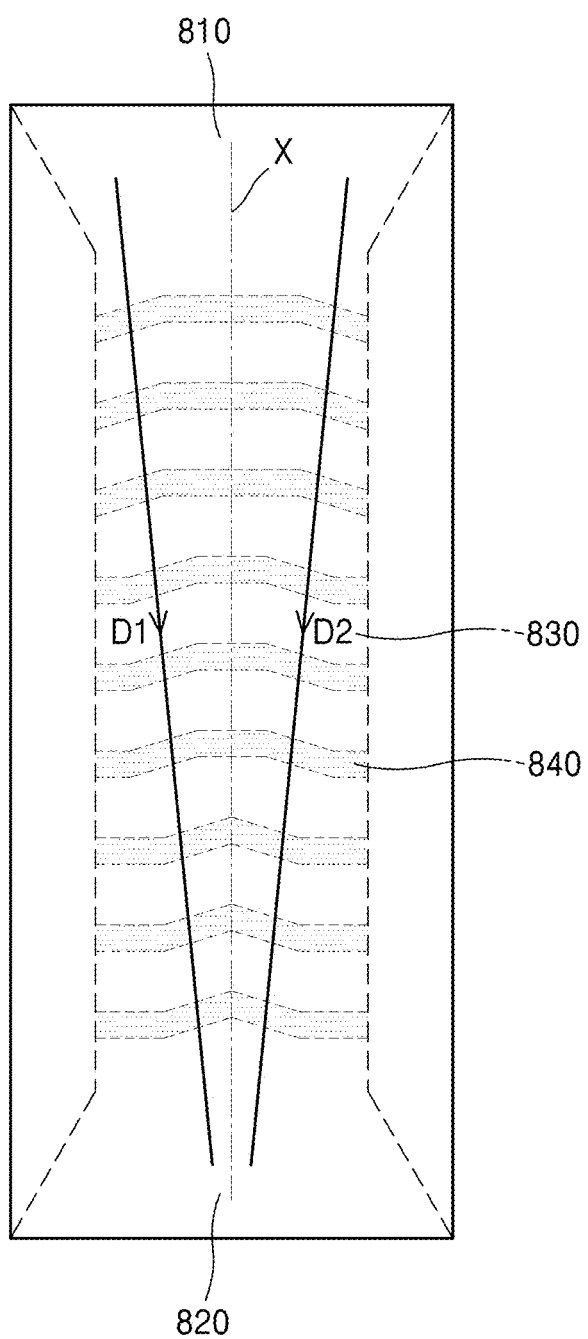
FIG. 8 is a view illustrating an apparatus for separating micro-particles according to another exemplary embodiment.

FIG. 8 is a view illustrating an apparatus 800 for separating micro-particles according to another exemplary embodiment. Referring to FIGS. 8 and 1, the arrangement shape and order of separating parts 840 illustrated in FIG. 8 are opposite those of the separating parts 140 illustrated in FIG. 1. That is, if the micro-particle separating apparatus 100 illustrated in FIG. 1 is inverted (or direction of fluid flow reversed in FIG. 1), the micro-particle separating apparatus 800 illustrated in FIG. 8 may be obtained. After critical particles P1 pass the micro-particle separating apparatus 800 of FIG. 8, the critical particles P1 may be discharged through a center region of an outlet 820. That is, although the same micro-particle separating apparatus is used, a region through which critical particles P1 are discharged may be changed according to the positioning or orientation of the micro-particle separating apparatus. Therefore, a user may determine a region through which target particles are discharged by changing the positioning or orientation of the micro-particle separating apparatus.

Figure 9:
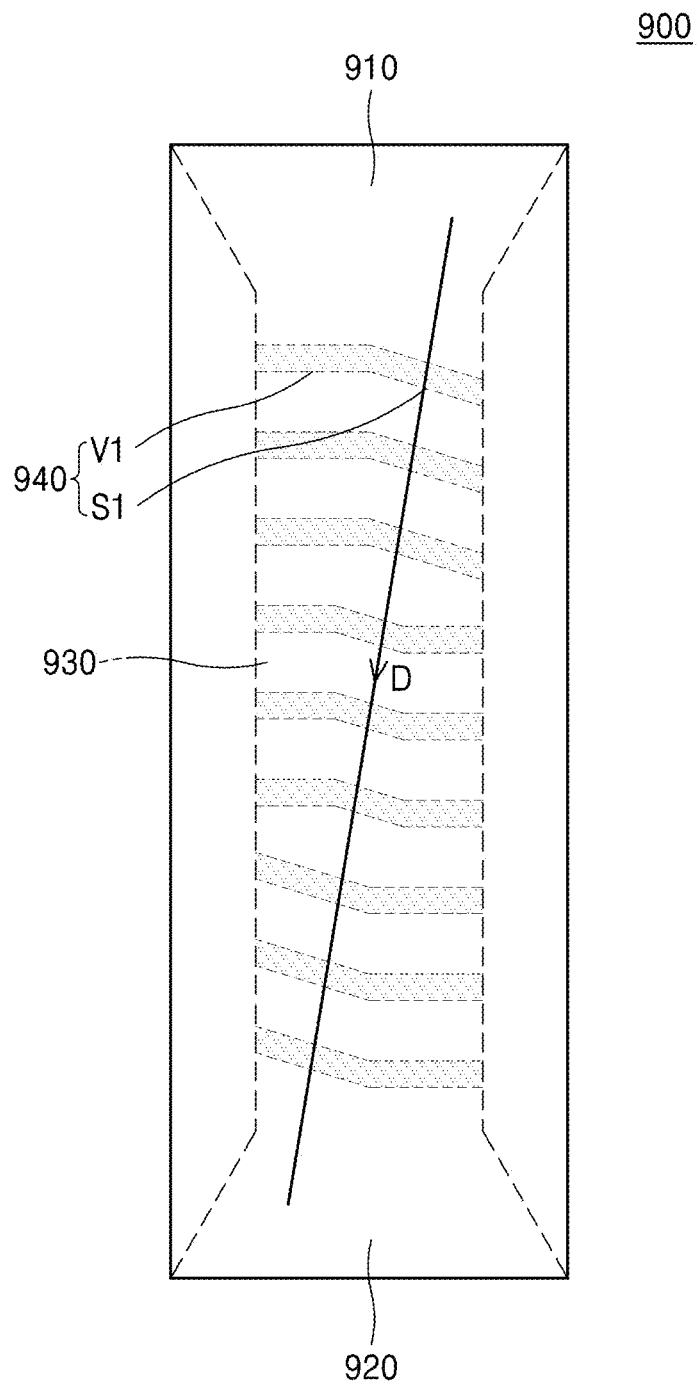
FIG. 9 is a view illustrating an apparatus for separating micro-particles according to another exemplary embodiment.

FIG. 9 is a view illustrating an apparatus 900 for separating micro-particles according to another exemplary embodiment. Referring to FIG. 9, the micro-particle separating apparatus 900 may include an inlet 910, an outlet 920, a channel 930, and one or more separating parts 940. Each of the more separating parts 940 may include at least one sub-slanted element S1. In the length direction L of the channel 930, the sub-slanted elements S1 may be sequentially arranged at predetermined intervals in a first direction D. For example, the first direction D may be a direction from a right region of the inlet 910 to a left region of the outlet 920. The first direction D and a slant direction of the sub-slanted elements S1 may have opposite signs. Therefore, critical particles having a diameter equal to or larger than ½ of the distance between a surface of the channel 930 and the sub-slanted elements S1 but smaller than the distance between the surface of the channel 930 and the sub-slanted elements S1 may be moved in the first direction D while passing across the separating parts 940.

Figure 10:
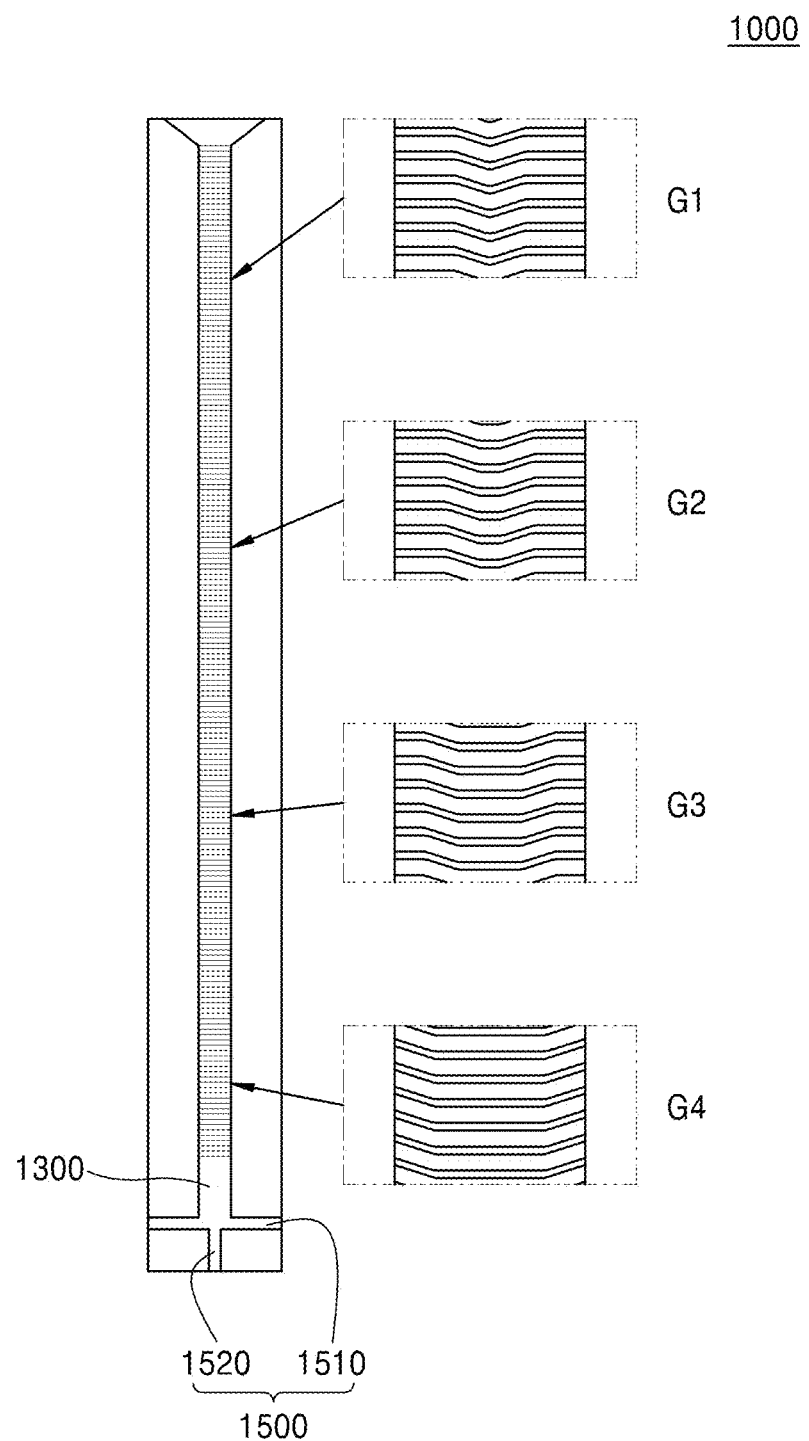
FIG. 10 is a view illustrating an apparatus for separating micro-particles according to another exemplary embodiment.

FIG. 10 is a view illustrating an apparatus 1000 for separating micro-particles according to another exemplary embodiment. Referring to FIG. 10, a plurality of separation groups G1, G2, G3, and G4 are arranged in a channel 1300. The separation groups G1, G2, G3, and G4 are similar to the separation groups G1, G2, and G3 illustrated in FIGS. 1 and 3A. A separation channel 1500 may be further disposed on an end of the channel 1300. For example, the separation channel 1500 may include a first sub-channel 1510 through which fluid containing critical particles P1 flows, and a second sub-channel 1520 through which fluid not containing the critical particles P1 flows. Although non-critical particles P2 may flow through the first sub-channel 1510, the concentration of non-critical particles P2 in the first sub-channel 1510 is much lower than the concentration of the critical particles P1. One of the first sub-channel 1510 and the second sub-channel 1520 may be connected to edge regions of the channel 1300, and the other of the first sub-channel 1510 and the second sub-channel 1520 may be connected to a center region of the channel 1300. For example, since the arrangement type of slanted elements illustrated in FIG. 10 is the same as the arrangement type of the slanted elements illustrated in FIG. 1, the first sub-channel 1510 may be connected to the edge regions of the channel 1300, and the second sub-channel 1520 may be connected to the center region of the channel 1300.

Figure 11:
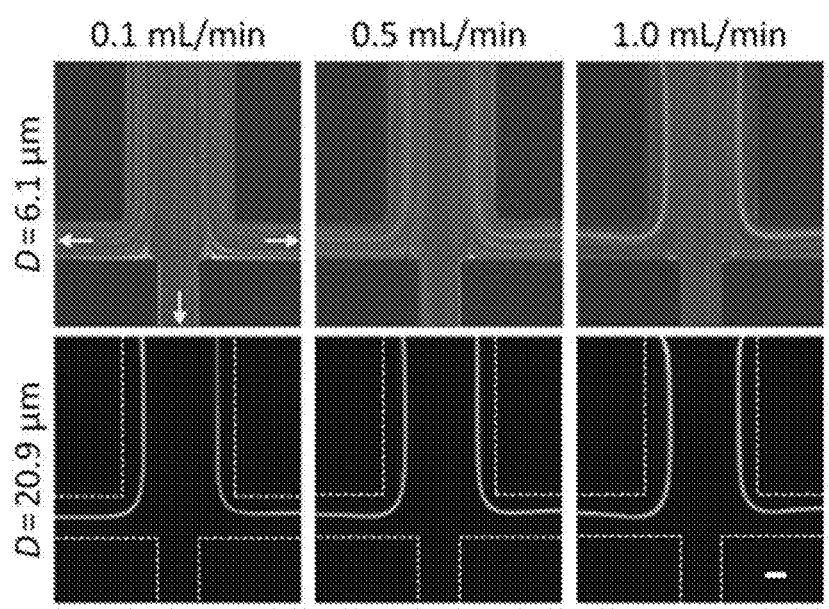
FIG. 11 is a view illustrating images of particles passing through a separation channel illustrated in FIG. 10.

The micro-particle separating apparatus 100 of the previous exemplary embodiments may concentrate critical particles P1 in a particular region regardless of the velocity of a fluid introduced into the channel 130. FIG. 11 is a view illustrating images of particles passing through the separation channel 1500 illustrated in FIG. 10. The micro-particle separating apparatus 1000 illustrated in FIG. 11 has the same channel and separating-part conditions as those of the micro-particle separating apparatus 100 explained with reference to FIGS. 7A and 7B.

Referring to FIG. 11, particles having a diameter of about 20.9 µm, that is, critical particles P1, are moved to the first sub-channel 1510 regardless of the velocity of fluid. Particles having a diameter of about 6.1 µm, that is, non-critical particles P2, are randomly moved to the first sub-channel 1510 and the second sub-channel 1520.

Figure 12:
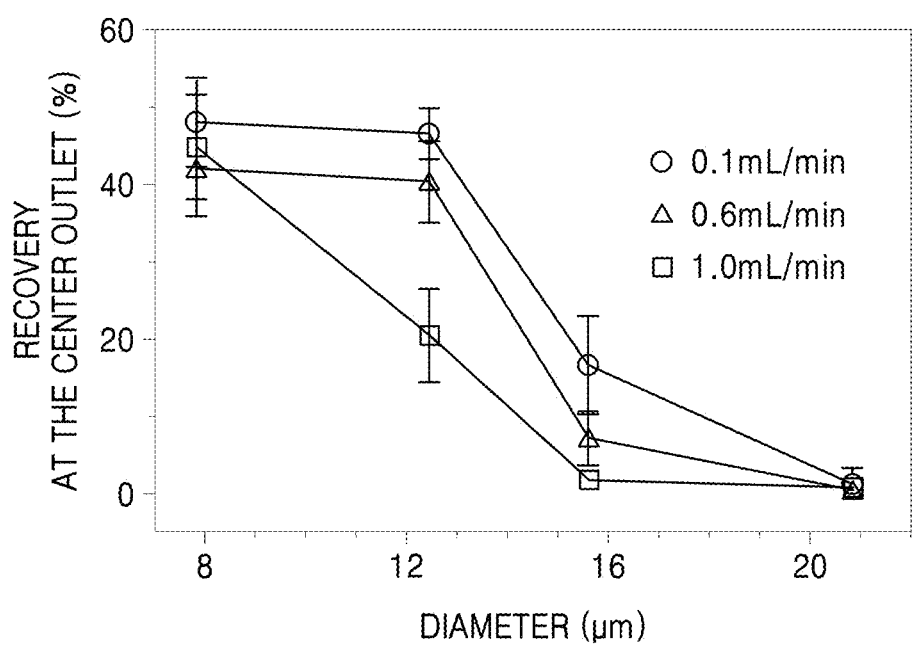
FIG. 12 is a graph illustrating the amount of particles passing through a second sub-channel illustrated in FIG. 10 with respect to the size of the particles.

FIG. 12 is a graph illustrating the amount of particles passing through the second sub-channel 1520 illustrated in FIG. 10 with respect to the size of the particles. The micro-particle separating apparatus 1000 used for FIG. 12 has the same channel and separating-part conditions as those of the micro-particle separating apparatus 100 explained with reference to FIGS. 7A and 7B. First particles having a diameter of about 8 µm, second particles having a diameter of about 12.5 µm, third particles having a diameter of about 15.5 µm, and fourth particles having a diameter of about 21 µm were included in a fluid. The fluid was introduced into the micro-particle separating apparatus 1000 at different velocities of 0.1 mL/min, 0.6 mL/min, and 1.0 mL/min, and then the fluid was detected in a center region of the micro-particle separating apparatus 1000.

Since the distance between a surface of the channel 1300 and slanted elements S of the micro-particle separating apparatus 1000 is about 39 µm, particles having a diameter of about 19.5 µm or greater are critical particles P1. That is, the four particles having a diameter of about 21 µm of the first to fourth particles are critical particles P1. Referring to FIG. 12, the fourth particles are not detected in a center region of an outlet regardless of the velocity of the fluid. That is, the fourth particles are discharged through edge regions of the outlet. Therefore, a fluid from which critical particles P1 are removed may be easily obtained regardless of the velocity of the fluid by using the micro-particle separating apparatus 1000 of the exemplary embodiment.

In the micro-particle separating apparatus 1000 of the exemplary embodiment, critical particles P1 are concentrated in a particular region such as edge regions of the outlet or the center region of the outlet regardless of the velocity of fluid. Therefore, an injector pump may not be necessary for precisely controlling the velocity of fluid. Therefore, after putting a sample in the micro-particle separating apparatus 1000 using a pipette or a syringe, e.g., manually, a user may easily separate critical particles P1 or non-critical particles P2 from the fluid.

Figure 13:
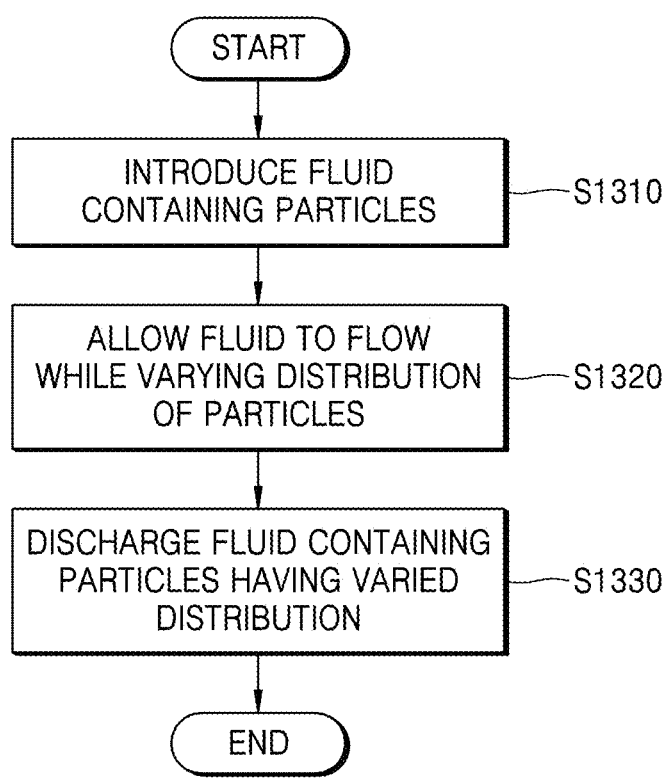
FIG. 13 is a flowchart illustrating a method of separating micro-particles using a micro-particle separating apparatus according to an exemplary embodiment.

FIG. 13 is a flowchart illustrating a method of separating micro-particles using the micro-particle separating apparatus 100 according to an exemplary embodiment.

A fluid containing critical particles P1 may be introduced into a channel 130 (S1310). For example, a user may hold the micro-particle separating apparatus 100 to align the length direction L (e.g., flow direction) of the channel 130 with the direction of gravity and may introduce the fluid through the inlet 110. Then, the fluid may be introduced into the channel 130 by gravity. Alternatively, a user may load a syringe with a sample containing cells and couple the syringe to the inlet 110 of the micro-particle separating apparatus 100. Then, the user may push a plunger of the syringe to inject the sample into the channel 130 of the micro-particle separating apparatus 100.

While the fluid flows in the channel 130 of the micro-particle separating apparatus 100, the distribution of particles of the fluid is varied by the separating parts 140 formed in the channel 130 (S1320). The separating parts 140 may include slanted elements S inclined toward the length direction L of the channel 130. The distribution of the particles may be varied according to the size of the particles and the distance d1 between a surface of the channel 130 and the slanted elements S. That is, particles having a diameter equal to or greater than ½ of the distance d1 between the slanted elements S and the surface of the channel 130 (that is, the critical particles P1) may be moved in a direction having a sign opposite to the sign of the slanted direction of the slanted elements S due to secondary fluid flows, and particles having a diameter smaller than ½ of the distance d1 (that is, non-critical particles P2) may be randomly moved.

If the channel 130 includes a plurality of separating parts 140, as the critical particles P1 move in the length direction of the channel 130, the critical particles P1 are concentrated in particular regions, that is, in regions defined by the arrangement of sub-slanted elements. In this manner, the distribution of the critical particles P1 is varied. If the distribution of the critical particles P1 is varied, the distribution of the non-critical particles P2 is varied relative to the distribution of the critical particles P1. For example, if the distribution of the critical particles P1 is concentrated in the edge regions of the channel 130, the distribution of the non-critical particles P2 is relatively increased in the center region of the channel 130.

The micro-particle separating apparatus 100 discharges the fluid including the critical particles P1 and the non-critical particles P2 from the channel 130 after the distributions of the critical particles P1 and the non-critical particles P2 are varied (S1330).

It should be understood that the micro-particle separating apparatus and the method of separating micro-particles using the micro-particle separating apparatus described herein according to the exemplary embodiments should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An apparatus for separating micro-particles, the apparatus comprising:
a channel through which a fluid flows along a length direction of the channel; and
a separating part protruding into the channel and including a slanted element inclined toward the length direction of the channel and a vertical element perpendicular to the length direction of the channel,
wherein the slanted element comprises first and second sub-slanted elements that are symmetric with respect to a center axis of the channel,
wherein the vertical element comprises:
a first sub-vertical element between the first sub-slanted element and a sidewall of the channel;
a second sub-vertical element between the second sub-slanted element and a sidewall of the channel; and
a third sub-vertical element between the first and second sub-slanted elements.

2. The apparatus of claim 1, wherein both ends of the separating part are connected to sidewalls of the channel.

3. The apparatus of claim 1, wherein a length direction of the slanted element is inclined toward the length direction of the channel.

4. The apparatus of claim 1, wherein the fluid comprises critical particles, and
a distance between the slanted element and a surface of the channel is greater than a diameter of the critical particles and equal to or smaller than twice the diameter of the critical particles.

5. The apparatus of claim 1, wherein the slanted element has a height greater than a distance between the slanted element and a surface of the channel.

6. The apparatus of claim 1, wherein the slanted element and the vertical element have the same height.

7. An apparatus for separating micro-particles, the apparatus comprising:
a channel through which a fluid flows; and
a separating part protruding into the channel and including a slanted element inclined toward a length direction of the channel and a vertical element perpendicular to the length direction of the channel, wherein the separating part comprises:
a first separating part comprising a first slanted element and a first vertical element; and
a second separating part separate from the first separating part in the length direction of the channel and comprising a second slanted element and a second vertical element.

8. The apparatus of claim 7, wherein the first slanted element and the second slanted element overlap each other in some regions of the channel and do not overlap each other in other regions of the channel.

9. The apparatus of claim 7, wherein the first slanted element comprises a first sub-slanted element inclined in a first direction, and the second slanted element comprises a second sub-slanted element inclined in the first direction.

10. The apparatus of claim 9, wherein an arrangement direction of the second sub-slanted element relative to the first sub-slanted element has a sign opposite to a sign of the first direction.

11. The apparatus of claim 9, wherein the first sub-slanted element and the second sub-slanted element have the same degree of slant and/or the same length.

12. The apparatus of claim 7, wherein first separating part is adjacent to an end of the channel, and the first slanted element is in contact with a sidewall of the channel or is in a center region of the channel.

13. An apparatus for separating micro-particles, the apparatus comprising:
a channel through which a fluid comprising particles flows; and
a plurality of slanted elements protruding into the channel and inclined toward a length direction of the channel, the plurality of slanted elements being separate from each other in the length direction of the channel, wherein the plurality of slanted elements are sequentially arranged in a first direction different from the length direction of the channel, wherein a subsequent one of the plurality of slanted elements is displaced along a direction perpendicular to the length direction relative to a previous one of the plurality of slanted elements.

14. The apparatus of claim 13, wherein the plurality of slanted elements each have a same slant direction.

15. The apparatus of claim 14, wherein the first direction and the slant direction have opposite signs.

16. The apparatus of claim 13, wherein the plurality of slanted elements comprises first and second sub-slanted elements that are symmetric with respect to a center axis of the channel.

17. The apparatus of claim 13, wherein two neighboring slanted elements of the plurality of slanted elements overlap each other in some regions and do not overlap each other in other regions in the length direction.

18. The apparatus of claim 13, wherein if particles having a diameter equal to or greater than ½ of a distance between at least one of the slanted elements and a surface of the channel but smaller than the distance are included in the fluid and introduced into the apparatus, the apparatus controls a moving direction of the particles so that the particles have directivity.

* * * * *